United States Patent [19]

Matzke et al.

[11] Patent Number: 5,663,150
[45] Date of Patent: Sep. 2, 1997

[54] CYCLOPENTANE-β-AMINO ACID TRIPEPTIDES

[75] Inventors: Michael Matzke, Wuppertal; Hans-Christian Militzer, Bergisch Gladbach; Joachim Mittendorf, Wuppertal; Franz Kunisch, Odenthal; Axel Schmidt, Wuppertal; Wolfgang Schönfeld, Wuppertal; Karl Ziegelbauer, Wuppertal, all of Germany

[73] Assignee: Bayer Aktiengesellschaft, Leverkusen, Germany

[21] Appl. No.: 679,038

[22] Filed: Jul. 12, 1996

[30] Foreign Application Priority Data

Jul. 19, 1995 [DE] Germany ............... 195 26 275.1

[51] Int. Cl.$^6$ .................. A61K 38/06; C07K 5/00; C07K 5/08
[52] U.S. Cl. .................. 514/18; 530/331; 514/19
[58] Field of Search .................. 514/18, 19; 530/331

[56] References Cited

FOREIGN PATENT DOCUMENTS 0 571 870 A1  12/1993  European Pat. Off. .
43 02 155 A1  7/1995   Germany .

OTHER PUBLICATIONS

Japanese Abstract of 021 747 53 A2, Fuji, Jul. 6, 1990.
J. Rudinger, "Characteristics of the Amino Acids as Components of a Peptide Hormone Sequence", *Peptide Hormones* (Univ. Park Press) 6/76 pp. 1–7.

*Primary Examiner*—Cecilia J. Tsang
*Assistant Examiner*—Bennett Celsa
*Attorney, Agent, or Firm*—Sprung Horn Kramer & Woods

[57] ABSTRACT

The present invention relates to cyclopentane-β-amino acid tripeptides, a process for their preparation and their use as antimicrobial, in particular antimycotic, medicaments.

9 Claims, No Drawings

CYCLOPENTANE-β-AMINO ACID TRIPEPTIDES

BACKGROUND OF THE INVENTION

1. Field of the Invention

The present invention relates to cyclopentane-β-amino acid tripeptides, to a process for their preparation and to their use as antimicrobial, in particular antimycotic, medicaments.

2. Description of the Related Art

The publications EP-A-571 870, DOS (German Offenlegungsschrift) 43 02 153 and JP 021 747 53 A2 disclose cyclopentane- and -pentene-β-amino acids having an antimicrobial and antibacterial action.

SUMMARY OF THE INVENTION

The present invention relates to cyclopentane-β-amino acid tripeptides of the general formula (I)

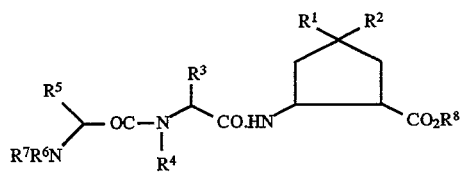

in which

R¹ and R² represent hydrogen, or

R¹ and R² together form a radical of the formula =CH₂,

R³ and R⁵ are identical or different and represent cycloalkyl having 3 to 8 carbon atoms or aryl having 6 to 10 carbon atoms or hydrogen, or represent straight-chain or branched alkyl having up to 8 carbon atoms, where the alkyl is optionally substituted by cyano, methylthio, hydroxyl, mercapto or guanidyl or by a group of the formula —NR⁹R¹⁰ or R¹¹—OC—, in which R⁹ and R¹⁰ independently of one another denote hydrogen, straight-chain or branched alkyl having up to 8 carbon atoms or phenyl, and R¹¹ denotes hydroxyl, benzyloxy, alkoxy having up to 6 carbon atoms or the abovementioned group —NR⁹R¹⁰, or the alkyl is optionally substituted by cycloalkyl having 3 to 8 carbon atoms or by aryl having 6 to 10 carbon atoms, which for its part is substituted by hydroxyl, halogen, nitro or alkoxy having up to 8 carbon atoms or by the group —NR⁹R¹⁰, in which R⁹ and R¹⁰ have the meanings given above, R⁴, R⁶ and R⁷ represent hydrogen, or R³ and R⁴ and/or R⁵ and R⁶ together form a radical of the formula —(CH₂)₃—, and R⁷ represents hydrogen, R⁸ represents hydrogen or straight-chain or branched alkyl having up to 6 carbon atoms or phenyl and racemates, diastereomeric forms and their salts.

The compounds according to the invention can also be present in the form of their salts. In general, salts with organic or inorganic bases or acids as well as internal salts may be mentioned here.

DESCRIPTION OF THE PREFERRED EMBODIMENTS

The acids which can be added preferably include hydrohalic acids, e.g. hydrochloric acid and hydrobromic acid, in particular hydrochloric acid, further phosphoric acid, nitric acid, sulphuric acid, mono- and bifunctional carboxylic acids and hydroxycarboxylic acids, e.g. acetic acid, maleic acid, malonic acid, oxalic acid, gluconic acid, succinic acid, fumaric acid, tartaric acid, citric acid, salicylic acid, sorbic acid and lactic acid as well as sulphonic acids, e.g. p-toluenesulphonic acid, 1,5-naphthalenedisulphonic acid or camphorsulphonic acid.

Physiologically acceptable salts can also be metal or ammonium salts of the compounds according to the invention which have a free carboxyl group. Those particularly preferred are, for example, sodium, potassium, magnesium or calcium salts, and also ammonium salts which are derived from ammonia or organic amines such as, for example, ethylamine, di- or triethylamine, di- or triethanolamine, dicyclohexylamine, dimethylaminoethanol, arginine, lysine, ethylenediamine or phenethylamine.

The compounds according to the invention can exist in stereoisomeric forms, for example either as image and mirror image (enantiomers), or not as image and mirror image (diastereomers), or as a diastereomer mixture or as pure cis-or trans-isomers. The invention relates both to the antipodes, racemic forms, diastereomer mixtures and the pure isomers. Like the diastereomers, the racemic forms can be separated into the stereoisomerically uniform constituents in a known manner. Separation into the stereoisomerically uniform compounds is carried out, for example, by means of diastereomeric esters and amides or on optically active phases. Crystallization of diastereomeric salts is additionally possible.

In the context of the invention, the amino acid radicals defined by the radical (—CO—CH(R³)—NR⁴—CO—CH(R⁵)—NR⁶R⁷—) are present in the L-form.

Preferred compounds of the general formula (I) are those in which

R¹ and R² represent hydrogen, or

R¹ and R² together form a radical of the formula =CH₂,

R³ and R⁵ are identical or different and represent hydrogen, straight-chain or branched alkyl having up to 6 carbon atoms, which is optionally substituted by phenyl, R⁴, R⁶ and R⁷ represent hydrogen, or R³ and R⁴ and/or R⁵ and R⁶ together form a radical of the formula —(CH₂)₃—, and R⁷ represents hydrogen, R⁸ represents hydrogen or straight-chain or branched alkyl having up to 4 carbon atoms and racemates, diastereomeric forms and their salts.

Particularly preferred compounds of the general formula (I) are those in which

R¹ and R² represent hydrogen, or

R¹ and R² together form a radical of the formula =CH₂,

R³ and R⁵ are identical or different and represent methyl or a group of the formula —CH(CH₃)—CH₂CH₃, R⁴, R⁶ and R⁷ represent hydrogen, or R³ and R⁴ and/or R⁵ and R⁶ together form a radical of the formula —(CH₂)₃—, and R⁷ represents hydrogen, R⁸ represents hydrogen, methyl or ethyl, and racemates, diastereomeric forms and their salts.

A process for the preparation of the compounds of the general formula (I) according to the invention has additionally been found, which is characterized in that compounds of the general formula (II)

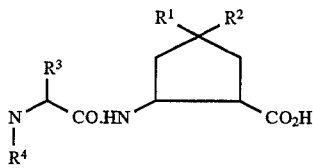

in which $R^1$, $R^2$, $R^3$ and $R^4$ have the meanings given above, are converted by reaction with protected amino acids of the general formula (III)

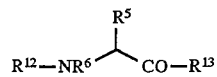

in which $R^5$ and $R^6$ have the meanings given above, $R^{12}$ represents a typical amino protective group, for example 9-fluorenyl-methoxycarbonyl, tert-butoxycarbonyl or benzyloxycarbonyl, preferably 9-fluorenylmethoxycarbonyl (Fmoc), and $R^{13}$ represents an activating protective group customary in peptide chemistry, preferably the hydroxysuccinimide ester radical, into the compounds of the general formula (IV)

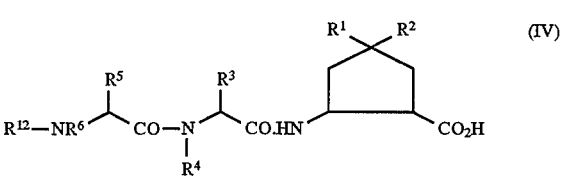

in which $R^1$, $R^2$, $R^3$, $R^4$, $R^5$, $R^6$ and $R^{12}$ have the meanings given above, in solvents and in the presence of a base, and then the amino protective group ($R^{12}$) is removed, and in the case of the esters ($R^8 \neq H$ in formula (I)) the acids are reacted by customary methods with the appropriate alcohols. The tripeptides can optionally be converted into their salts in a customary manner.

The process according to the invention can be illustrated by way of example by the following reaction scheme:

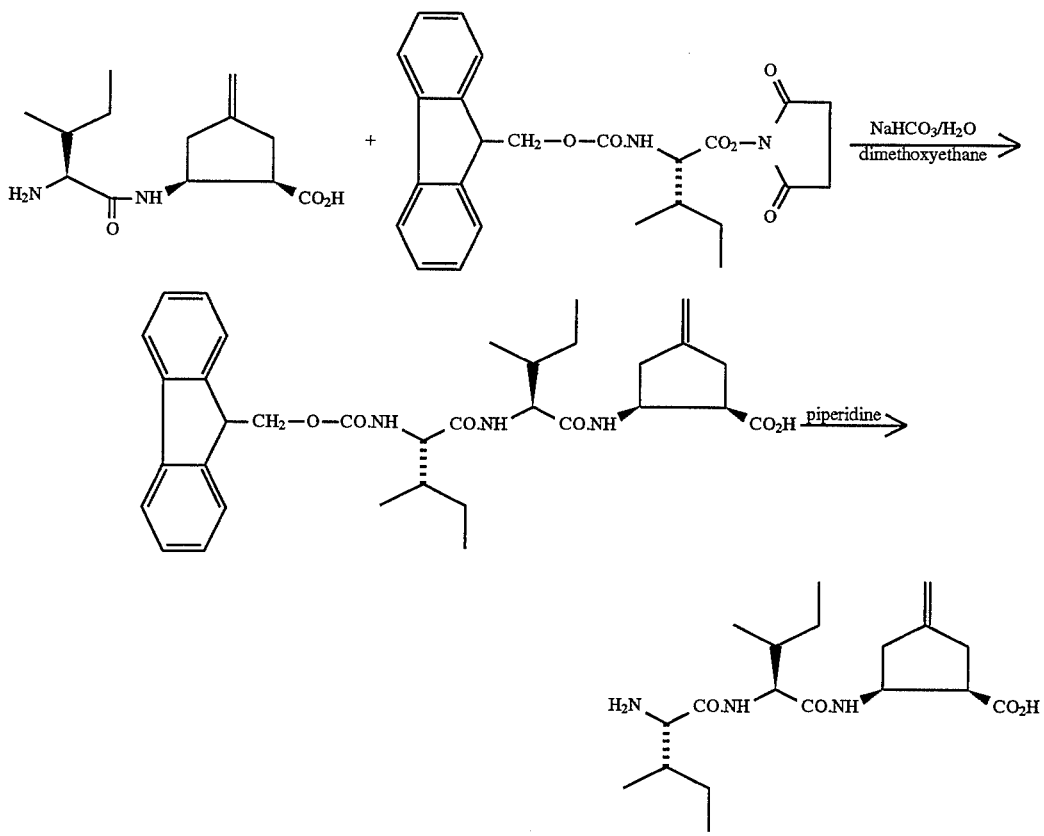

Amino protective groups in the context of the invention are the customary amino protective groups used in peptide chemistry.

These preferably include: benzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxycarbonyl, 2-nitro-4,5-dimethoxybenzyloxycarbonyl, methoxycarbonyl, ethoxycarbonyl, tert-butoxycarbonyl, allyloxycarbonyl, vinyloxycarbonyl, 3,4,5-trimethoxybenzyloxycarbonyl, phthaloyl, 2,2,2-trichloroethoxycarbonyl 2,2,2-trichloro-tert-butoxycarbonyl, menthyloxycarbonyl, 4-nitrophenoxycarbonyl, fluorenyl-9-methoxycarbonyl (Fmoc), formyl, acetyl, propionyl, pivaloyl, 2-chloroacetyl, 2-bromoacetyl, 2,2,2-trifluoroacetyl, 2,2,2-trichloroacetyl, benzoyl, benzyl, 4-chlorobenzoyl, 4-bromobenzoyl, 4-nitrobenzoyl, phthalimido, isovaleroyl or benzyloxymethylene, 4-nitrobenzyl, 2,4-dinitrobenzyl, 4-nitrophenyl or 2-nitrophenylsulphenyl. The Fmoc group is particularly preferred.

Suitable carboxyl radicals ($R^{13}$) are in general adducts with carbodiimides, e.g. N,N'-diethyl-, N,N'-diisopropyl- or N,N'-dicyclohexylcarbodiimide, N-(3-dimethylaminoisopropyl)-N'-ethylcarbodiimide hydrochloride, N-cyclohexyl-N'(2-morpholinoethyl) carbodiimide metho-p-toluenesulphonate, or carbonyl compounds such as carbonyldiimidazole, or 1,2-oxazolium compounds such as 2-ethyl-5-phenyl-1,2-oxazolium-3-sulphate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or benzotriazolyloxy-tris (dimethylamino)phosphonium hexafluorophosphate, 1-hydroxybenzotriazole or hydroxysuccinimide ester. The hydroxysuccinimide ester is preferred.

Suitable solvents are the customary organic solvents which do not change under the reaction conditions. These preferably include ethers such as diethyl ether, dioxane, tetrahydrofuran, glycol dimethyl ether, dimethoxyethane or hydrocarbons such as benzene, toluene, xylene, hexane, cyclohexane, or petroleum fractions or dimethylformamide. It is also possible to use mixtures of the solvents mentioned. Tetrahydrofuran, diethyl ether and dimethoxyethane are preferred. It is additionally possible to employ water or mixtures of the abovementioned solvents with water.

Additionally, for example, alkali metal carbonates, e.g. sodium or potassium carbonate or hydrogen carbonate, or organic bases such as trialkylamines, e.g. triethylamine, ethyldiisopropylamine, N-ethylmorpholine, N-methylpiperidine or N-methylmorpholine can be employed. N-Methylmorpholine is preferred.

The auxiliaries and bases are employed in an amount from 1.0 mol to 3.0 mol, preferably 1.0 mol to 1.2 mol, relative to 1 mol of the compounds of the general formula (III).

The reactions are carried out in a temperature range from 0° C. to 100° C., preferably at 0° C. to 3° C. and at normal pressure.

The reactions can be carried out both at normal pressure and at elevated or reduced pressure (for example 0.5 to 5 bar), preferably at normal pressure.

In general, the amino protective group is removed in a manner known per se under acidic or basic conditions, or reductively by catalytic hydrogenation, for example With Pd/C inorganic solvents such as ethers, e.g. tetrahydrofuran or dioxane, or alcohols, e.g. methanol, ethanol or isopropanol.

Hydrogenation is in general carried out in a temperature range from 0° C. to 80° C., preferably from 0° C. to 40° C.

In general, the hydrogenation is carried out at elevated pressure from 2 bar to 8 bar, preferably from 3 to 5 bar.

For removal of the amino protective group ($R^{12}$=Fmoc), suitable bases are, for example, piperidine, morpholine, dicyclohexylamine, p-dimethylaminopyridine, diisopropylethylamine or piperazine. Piperidine is preferred.

The auxiliaries and bases are employed in an amount from 1.0 mol to 3.0 mol, preferably 1.0 mol to 1.2 mol, relative to 1 mol of the compounds of the general formula (IV).

The reactions are carried out in a temperature range from 0° C. to 100° C., preferably at 0° C. to 30° C. and at normal pressure.

The reactions can be carried out both at normal pressure and at elevated or reduced pressure (for example 0.5 to 5 bar), preferably at normal pressure.

The compounds of the general formula (II) are known in some cases or are new and can in this case be prepared by reaction of the free β-amino acid of the general formula (V)

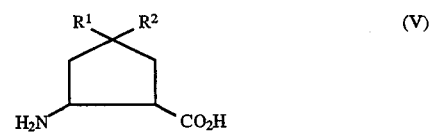

in which
$R^1$ and $R^2$ have the meanings given above, with the amino acids of the general formula (VI)

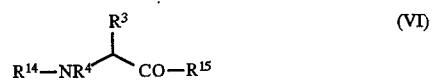

in which
$R^3$ and $R^4$ have the meanings given above,
$R^{14}$ has the meaning of $R^{12}$ given above and is identical to or different from this,
$R^{15}$ has the meaning of $R^{13}$ given above and is identical to or different from this, or
$R^{14}$ and $R^{15}$ together represent the grouping

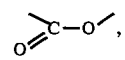

in analogy to the abovementioned processes and under identical conditions.

The compounds of the general formulae (III), (V) and (VI) are known per se.

The compounds of the general formula (IV) are new and can be prepared as described above.

The above preparation processes are only given for clarification. The preparation of the compounds of the general formula (I) according to the invention is not restricted to these processes and any modification of these processes can be used in an identical manner for the preparation.

The compounds according to the invention exhibit an unforeseeable, useful spectrum of pharmacological action.

The compounds of the general formula (I) according to the invention and their acid addition salts have antimicrobial, in particular strongly antimycotic, actions. They have a wide spectrum of antimycotic action against dermatophytes, such as *Trichophyton mentagrophytes* and *Microsporon canis*, against yeast fungi such as *Candida albicans, Candida glabrata, Epidermophyton floccosum* and against mould fungi such as *Aspergillus niger* and *Aspergillus fumigatus*. The enumeration of these microorganisms in no way represents a restriction of the microorganisms which can be controlled, but is only of illustrative character. The compounds are therefore suitable for the treatment of dermatomycoses and systemic mycoses.

Testing of in-vivo activity

The test model for antimycotic in-vivo actions used was systemic mouse candidias is:

Male $CFW_1$ mice of weight 20 g were infected in the tail vein by injection of $3 \times 10^5$ CFU of *C. albicans* per animal.

Untreated control animals died completely within one week post-infectionem (p.i.) of a generalized candidiasis with granuloma formation in the kidneys. For activity testing, the preparations, dissolved in a 0.2% strength aqueous glucose-agar solution, were administered orally by stomach tube to the infected animals twice daily.

The daily doses were 2×50 mg/kg of body weight (BW), the treatment period was 5 days.

The survival rates of the treated animals were noted daily up to the 10th day p.i. In the case of the untreated control animals, no animals survived at this point.

For the preparations, 10 animals each were employed per dose and control group.

The results are shown in Table A.

TABLE A

| Ex. No. | Dose [mg/kg, 2 × daily] | Administration | Number of surviving animals |
|---------|-------------------------|----------------|-----------------------------|
| Control |                         |                | 0/10                        |
| 1       | 50                      | p.o.           | 8/10                        |

Alternatively, the in-vivo activity can also be tested on Wistar rats. The test is in this case carried out as follows:

Eight-week old, specifically pathogen-free, male Wistar rats of weight 200 g are infected via the lateral tail vein with $5 \times 10^6$ CFU of *Candida albicans* in 0.5 ml of PBS. This leads to a 100% mortality within eight days. Even one day after infection, the animals exhibit haemorrhages in the medial canthus; besides the kidneys other organ systems such as the brain, heart, liver, spleen, retina and lungs are affected. Administration of substance is carried out orally twice daily over five days in 1 ml each of glucose (5%)-agar (0.2%) solution beginning on the day of infection.

These useful properties make possible the use of the compounds according to the invention as chemotherapeutic active compounds in medicine and as substances for the preservation of inorganic and organic materials, in particular of organic materials of all types, e.g. polymers, lubricants, dyes, fibres, leather, paper and wood, foodstuffs and water. The compounds according to the invention can furthermore be employed as fungicidal active compounds, in particular for the control of fungal infections in plants.

The present invention includes pharmaceutical preparations which, besides non-toxic, inert pharmaceutically suitable excipients and auxiliaries, contain one or more compounds according to the invention or which consist of one or more active compounds according to the invention, and processes for the production of these preparations.

The active compound or compounds can optionally also be present in microencapsulated form in one or more of the excipients stated above.

Preferred pharmaceutical preparations which may be mentioned are tablets, coated tablets, capsules, pills, granules, suppositories, solutions, suspensions and emulsions, pastes, ointments, gels, creams, lotions, powders and sprays.

The therapeutically active compounds should be present in the abovementioned pharmaceutical preparations in a concentration of approximately 0.1 to 99.5, preferably of approximately 0.5 to 95,% by weight of the total mixture.

Apart from the compounds according to the invention, the abovementioned pharmaceutical preparations can also contain other pharmaceutical active compounds.

In general, it has proved advantageous both in human and in veterinary medicine to administer the active compound or compounds according to the invention in total amounts of approximately 0.5 to approximately 500, preferably 5 to 100, mg/kg of body weight every 24 hours, if appropriate in the form of several individual doses, to achieve the desired results. An individual dose preferably contains the active compound or compounds according to the invention in amounts from approximately 1 to approximately 80, in particular 3 to 30, mg/kg of body weight.

STARTING COMPOUND

Example I 1,2-cis-2-(N-(9-Fluorenylmethoxycarbonyl)-(S)-isoleucyl)-(S)-isoleucyl)-amino-4-methylenecyclopentane-1-carboxylic acid

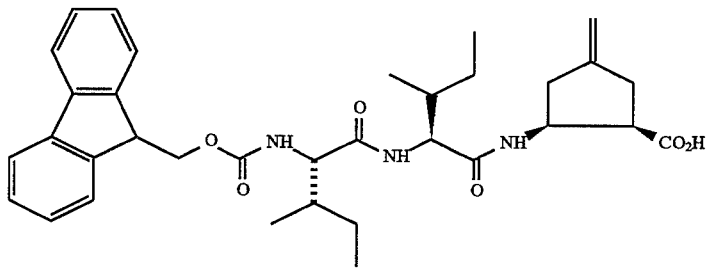

A solution of N-(9-fluorenylmethoxycarbonyl)-(S)-isoleucine hydroxysuccinimide ester (4.5 g, 10 mmol) in 80 ml of dimethoxyethane is added dropwise at room temperature to a solution of (+)-1,2-cis-2-(S)-isoleucyl-amino-4-methylene-cyclopentane-1-carboxylic acid (2.54 g, 10 mmol) and sodium hydrogencarbonate (966 mg, 11.5 mmol) in 40 ml of water. The reaction mixture is stirred at room temperature for 15 h. It is then acidified to pH 2 using dilute hydrochloric acid and extracted several times with diethyl ether. The combined organic phases are dried over sodium sulphate and concentrated in vacuo. The product is crystallized from diethyl ether/petroleum ether.

Yield: 5.1 g (88% of theory)

M.p.: 185°–187° C.

$^1$H-NMR (200 MHz, DMSO-$D_6$): δ=0.70–0.90 (m, 12H); 0.95–1.20; 1.28–1.55; 1.59–1.88 (3m, 6H); 2.25–2.80 (m, 4H); 3.25–3.5 (m, 2H); 3.97 (cm, 1H); 4.05–4.36 (m, 4H); 4.79 (cm, 2H); 7.25–7.94 (m, 11H). $C_{34}H_{43}N_3O_6$ (589.7)

PREPARATION EXAMPLE

Example 1

(−)-1,2-cis-(2-((S)-Isoleucyl)-(S)-isoleucylamino)-4-methylenecyclopentane-1-carboxylic acid

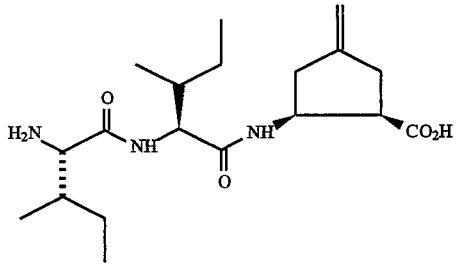

A solution of the compound from Example I (5 g, 8.5 mmol) in piperidine (25 ml) is stirred at room temperature for 1 h. The piperidine is then distilled off in vacuo and the residue is taken up in water. After extraction several times with diethyl ether, the aqueous phase is concentrated in vacuo. The residue is filtered through a silica gel column (dichloromethane/methanol, 9:1→3:1) and the product is crystallized from isopropanol/diethyl ether.

Yield: 1.5 g (48% of theory)

M.p.: 168°–170° C.

$[\alpha]^{20}_D = -7.55$ (c=1.0 in water)

$^1$H-NMR (200 MHz, D$_2$O): δ=0.68–0.81 (m, 12H); 0.90–1.14; 1.17–1.45; 1.46–1.80 (3m, 6H); 2.27 (dd, 1H); 2.42–2.61 (m, 3H); 2.84 (cm, 1H); 3.26 (d, 1H); 3.98 (d, 1H); 4.24 (cm, 1H); 4.83 (cm, 1H). C$_{19}$H$_{33}$N$_3$O$_4$(367.4)

We claim:

1. A cyclopentane-β-amino acid tripepride of the formula (I):

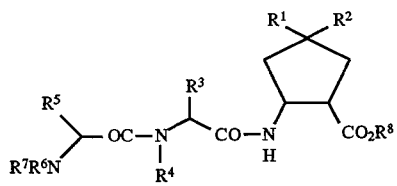

in which

R$^1$ and R$^2$ represent hydrogen; or

R$^1$ and R$^2$ together form a radical of the formula =CH$_2$;

R$^3$ and R$^5$ are identical or different and represent hydrogen or straight-chain or branched alkyl having 1 to 6 carbon atoms;

R$^4$, R$^6$ and R$^7$ represent hydrogen; and

R$^8$ represents hydrogen or straight-chain or branched alkyl having 1 to 6 carbon atoms; in the form of the racemic mixture, a diastereomer or a salt thereof.

2. A fungicidal composition comprising a fungicidally effective amount of a cyclopentane-β-amino acid tripeptide according to claim 1 and a carrier.

3. A method of preserving an inorganic or organic material or mixtures thereof comprising adding to said material a fungicidally effective amount of a cyclopentane-β-amino acid tripeptide according to claim 1.

4. The method according to claim 3, wherein said material is selected from the group consisting of polymers, lubricants, dyes, fibers, leather, paper, wood, foodstuffs and water.

5. A method of protecting plants comprising applying to the plants or to the area around the plants a fungicidally effective amount of a cyclopentane-β-amino acid tripepride according to claim 1.

6. A method of treating a fungi infection in an animal or human in need thereof comprising administering to said animal or human a fungicidally effective amount of a cyclopentane-β-amino acid tripeptide according to claim 1.

7. Tripeptides of the formula (I) according to claim 1, in which

R$_3$ and R$^5$ are identical or different and represent methyl or a group of the formula —CH(CH$_3$)—CH$_2$CH$_3$, R$^8$ represents hydrogen, methyl or ethyl, and racemates, diastereomeric forms and their salts.

8. Process for the preparation of tripeptides of claim 1 comprising reacting compounds of the formula (II)

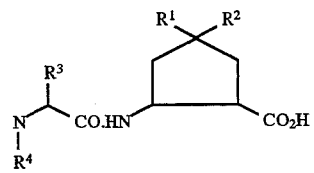

with protected amino acids of the formula (III)

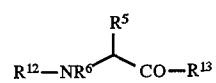

in which

R$^{12}$ represents an amino protective group and

R$^{13}$ represents an activating protective group, to form compounds of the formula (IV)

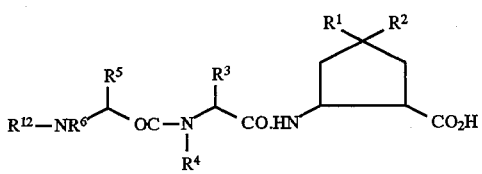

in solvents and in the presence of a base, removing the amino protective group (R$^{12}$), optionally in the case of the esters (R$^8$≠H in formula (I)) reacting the acids with an alcohol having an alkyl group falling within the definition of R$^8$ and, if present separating stereoisomers, and optionally converting the tripeptides into their salts.

9. Compounds of the formula (IV)

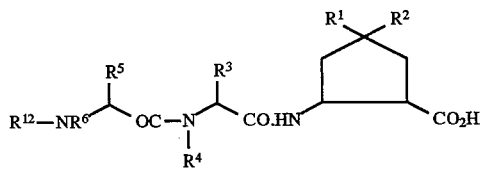

in which

R$^1$ and R$^2$ represent hydrogen, or

R$^1$ and R$^2$ together form a radical of the formula =CH$_2$,

R$^3$ and R$^5$ are identical or different and represent hydrogen, or represents straight-chain or branched alkyl having up to 6 carbon atoms, R$^4$, and R$^6$ represent hydrogen, and R$^{12}$ represents an amino protective group.

* * * * *